US011576996B2

(12) United States Patent
Ohe et al.

(10) Patent No.: US 11,576,996 B2
(45) Date of Patent: Feb. 14, 2023

(54) DISCHARGE DEVICE AND ELECTRIC MACHINE FOR IMPROVING EFFICIENCY OF REACTIVE SPECIES

(71) Applicant: SHARP KABUSHIKI KAISHA, Osaka (JP)

(72) Inventors: Nobuyuki Ohe, Sakai (JP); Tetsuya Ezaki, Sakai (JP); Satoshi Okano, Sakai (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 662 days.

(21) Appl. No.: 16/500,087

(22) PCT Filed: Aug. 25, 2017

(86) PCT No.: PCT/JP2017/030553
§ 371 (c)(1),
(2) Date: Oct. 1, 2019

(87) PCT Pub. No.: WO2018/189928
PCT Pub. Date: Oct. 18, 2018

(65) Prior Publication Data
US 2021/0128775 A1    May 6, 2021

(30) Foreign Application Priority Data
Apr. 10, 2017  (JP) .............................. JP2017-077421

(51) Int. Cl.
*A61L 9/22*   (2006.01)
*H01T 19/04*  (2006.01)
*H01T 23/00*  (2006.01)

(52) U.S. Cl.
CPC ................ *A61L 9/22* (2013.01); *H01T 19/04* (2013.01); *H01T 23/00* (2013.01)

(58) Field of Classification Search
CPC .. H01J 27/02; H01J 27/20; H01J 27/22; H01J 27/24; H01J 27/26; F24F 8/30; F24F 7/00;
(Continued)

(56) References Cited

U.S. PATENT DOCUMENTS 10,910,186 B2 *  2/2021  Nishida ................... H01J 27/26
10,980,909 B2 *  4/2021  Okano ....................... A61L 9/22
(Continued)

FOREIGN PATENT DOCUMENTS

JP    2013225383 A  * 10/2013
JP    2014032783 A  *  2/2014
(Continued)

*Primary Examiner* — Jared Fureman
*Assistant Examiner* — Nicolas Bellido
(74) *Attorney, Agent, or Firm* — ScienBiziP, P.C.

(57) ABSTRACT

Provided is a discharge device that can improve the efficiency of generating reactive species. A discharging unit that discharges in response to an application of a voltage protrudes from a housing. The discharging unit is disposed in a duct through which gas flows. An upstream support is disposed upstream of the discharging unit in a direction of gas flow without overlapping the discharging unit. The upstream support protrudes further from the housing than the discharging unit. The upstream support includes a root portion joined to the housing. The root portion includes a widened portion that is disposed in the duct and that protrudes toward the discharging unit when viewed in the direction of gas flow.

8 Claims, 9 Drawing Sheets

(58) Field of Classification Search
CPC ... F24F 2003/1682; F24F 3/166; H01T 19/00; H01T 19/04; H01T 23/00; H01T 19/02; B60H 3/0071; B60H 3/0078; A61L 9/22; B03C 2201/06; B03C 3/38; B03C 3/40; B03C 3/41; B03C 3/74; B03C 3/743; B65H 2301/5133; C01B 13/11; C02F 1/4608; G03G 15/0291; H05F 3/04; H05H 2001/481
See application file for complete search history.

(56) References Cited

U.S. PATENT DOCUMENTS

| | | | | |
|---|---|---|---|---|
| 2016/0104595 | A1* | 4/2016 | Nishida | H01J 27/022 |
| | | | | 313/230 |
| 2016/0204581 | A1* | 7/2016 | Nishida | H01T 23/00 |
| | | | | 250/423 F |
| 2017/0316910 | A1 | 11/2017 | Nishida et al. | |
| 2018/0053620 | A1* | 2/2018 | Nishida | H01J 27/26 |
| 2018/0053621 | A1* | 2/2018 | Nishida | H01J 27/22 |
| 2020/0054780 | A1* | 2/2020 | Ezaki | A61L 9/22 |

FOREIGN PATENT DOCUMENTS

| | | | | | |
|---|---|---|---|---|---|
| JP | | 2015-005387 A | | 1/2015 | |
| JP | | 2016-054099 A | | 4/2016 | |
| JP | | 2016054099 A | * | 4/2016 | ............ A61L 9/22 |
| JP | | 2017-033883 A | | 2/2017 | |
| WO | WO-2015151309 A1 | * | 10/2015 | ............ B03C 3/38 |
| WO | WO-2017010113 A1 | * | 1/2017 | ............ A61L 9/22 |
| WO | | 2017/022256 A1 | | 2/2017 | |

\* cited by examiner

DISCHARGE DEVICE AND ELECTRIC MACHINE FOR IMPROVING EFFICIENCY OF REACTIVE SPECIES

TECHNICAL FIELD

The present disclosure relates to a discharge device and an electric machine. The present disclosure claims priority to Japanese Patent Application No. 2017-077421 filed in the Japan Patent Office on Apr. 10, 2017. The entire contents of which are incorporated herein by reference.

BACKGROUND ART

Ion generators have been used for such purposes as purifying, sterilizing, or deodorizing air in a room. Ion generators generally include a discharge electrode that generates ions through discharging.

Japanese Unexamined Patent Application Publication No. 2015-5387 (PTL 1) discloses an electrode protector that protects a needle electrode that generates ions through discharging. The electrode protector includes a first protection portion and a second protection portion, which protrude further from a housing than the tip of the needle electrode and oppose each other on both sides of the needle electrode while having a gap therebetween.

CITATION LIST

Patent Literature

PTL 1: Japanese Unexamined Patent Application Publication No. 2015-5387

SUMMARY OF INVENTION

Technical Problem

Discharge devices that generate reactive species such as ions through discharging are required to increase the quantity of reactive species generated by an application of the same voltage to improve the efficiency of generating reactive species.

The present disclosure provides a discharge device that can improve the efficiency of generating reactive species.

Solution to Problem

The present disclosure provides a discharge device that includes a housing, a discharging unit that discharges in response to an application of a voltage, and a protruding unit. The discharging unit protrudes from the housing. The discharging unit is disposed in a duct through which gas flows. The protruding unit is disposed upstream of the discharging unit in a direction of gas flow without overlapping the discharging unit. The protruding unit protrudes further from the housing than the discharging unit. The protruding unit includes a root portion joined to the housing. The root portion includes a widened portion that is disposed in the duct and that protrudes toward the discharging unit when viewed in the direction of gas flow.

In the above discharge device, the discharging unit includes a plurality of linear electric conductors and a base portion that bundles the electric conductors.

In the above discharge device, when viewed in the direction in which the gas flows, a minimum distance between the protruding unit and an end portion of the base portion on a side of the base portion from which the electric conductor protrudes is larger than a length by which the electric conductor protrudes from the base portion.

In the above discharge device, the widened portion is disposed closer to the housing than an end portion of the base portion on a side of the base portion from which the electric conductor protrudes.

In the above discharge device, a surface of the protruding unit curves from an upstream side in the direction in which the gas flows toward the discharging unit to protrude outward.

In the above discharge device, the root portion includes a second widened portion that protrudes away from the discharging unit when viewed in the direction in which the gas flows.

The above discharge device further includes a second protruding unit that is disposed while having the discharging unit interposed between the second protruding unit and the protruding unit when viewed in the direction in which the gas flows, the second protruding unit protruding further from the housing than the discharging unit.

Advantageous Effects of Invention

The discharge device according to the present disclosure can improve the efficiency of generating reactive species.

DESCRIPTION OF EMBODIMENTS

Embodiments will be described below with reference to the drawings. The same or equivalent components are denoted with the same reference signs, and may not be described repeatedly.

First Embodiment

[Air Cleaner 100]

Figure 1:
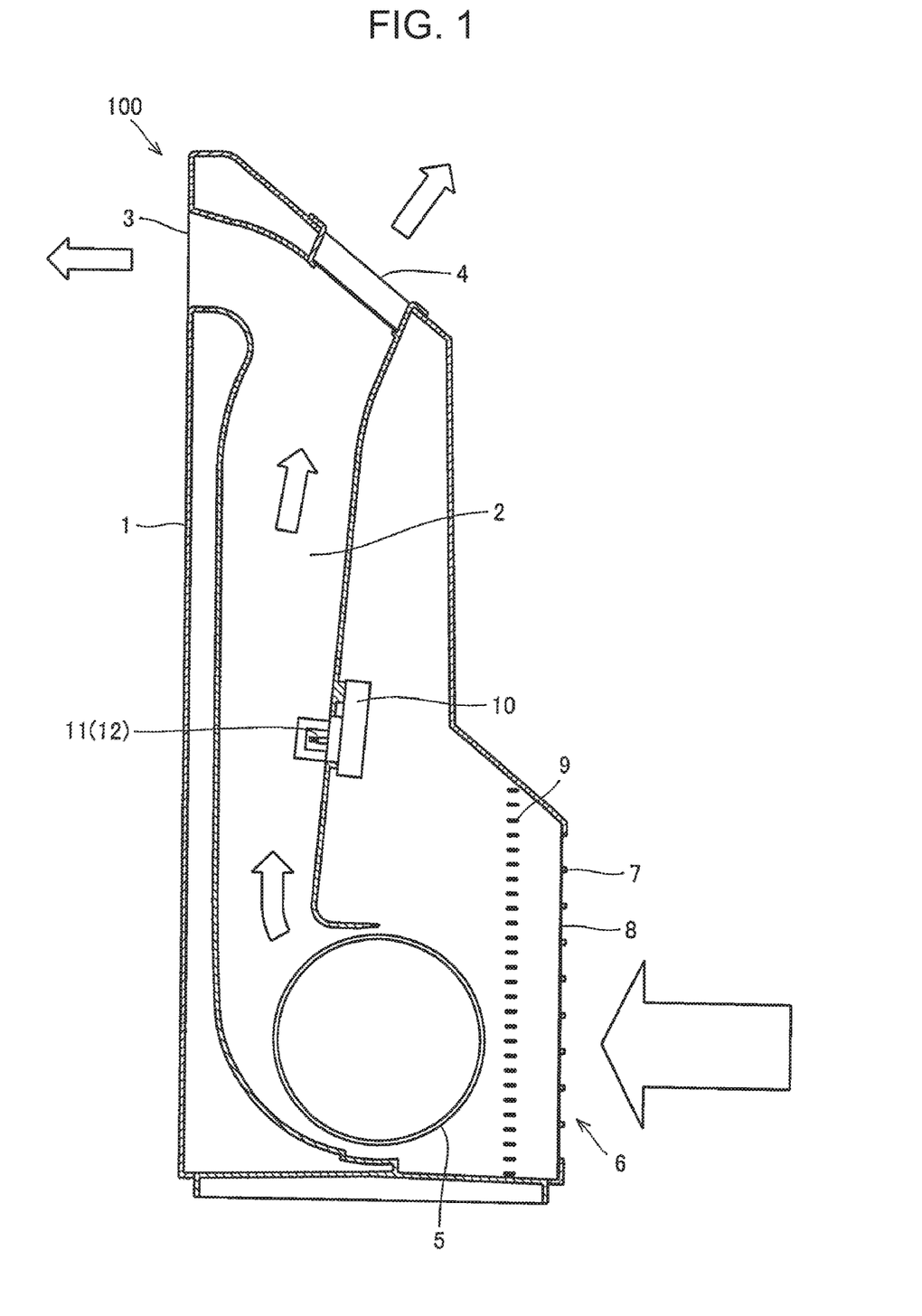
FIG. 1 is a cross-sectional view of a schematic structure of an air cleaner including a discharge device according to an embodiment.

FIG. 1 is a cross-sectional view of a schematic structure of an air cleaner 100 including a discharge device 10 according to an embodiment. The air cleaner 100 includes an outer casing 1, which forms the exterior of the air cleaner 100. The left side in FIG. 1 corresponds to the front side of the air cleaner 100 or the front side of the outer casing 1. The right side in FIG. 1 corresponds to the rear side of the air cleaner 100 or the rear side of the outer casing 1.

A duct 2 vertically extends inside the outer casing 1. Hollow arrows in FIG. 1 denote the directions in which gas, typically, air flows in the duct 2. A first outlet 3 and a second outlet 4 are formed at an upper portion of the outer casing 1. The first outlet 3 is formed in the front surface at the upper portion of the outer casing 1. The second outlet 4 is formed in the rear surface at the upper portion of the outer casing 1. The first outlet 3 and the second outlet 4 are disposed at the upper end of the duct 2. The first outlet 3 and the second outlet 4 are disposed at the downstream end in the direction in which air flows in the duct 2. The duct 2 is open to the outside of the outer casing 1 at the first outlet 3 and the second outlet 4.

A blower 5 is disposed in an upstream end opening of the duct 2. The blower 5 is disposed at a lower portion of the outer casing 1. The blower 5 is disposed in a lower end opening of the duct 2. The blower 5 delivers gas sucked through an inlet port 6 into the duct 2. The blower 5 is, for example, a cross flow fan, but not particularly limited to this.

The inlet port 6 is formed in the rear surface at a lower portion of the outer casing 1. A resin-made gridlike grille 7 is disposed at the inlet port 6. A thin mesh filter 8 is attached to the inner side of the grille 7. A fan guard 9 is disposed behind the filter 8 (on the inner side of the outer casing 1). The fan guard 9 is disposed between the inlet port 6 and the blower 5. The fan guard 9 is disposed to prevent foreign matter from entering the blower 5. The upstream end of the duct 2 in the direction in which air flows in the duct 2 is disposed to face the inlet port 6 with the fan guard 9 interposed therebetween.

The discharge device 10 is disposed at a center portion of the duct 2 in the vertical direction. The discharge device 10 is disposed between the upper end and the lower end of the duct 2. The discharge device 10 is attached to the wall surface of the duct 2 on the rear surface. The discharge device 10 may be disposed at any portion between the upstream end and the downstream end in the direction in which air flows in the duct 2, instead of being attached to the wall surface of the duct 2 on the rear surface, as illustrated in FIG. 1. For example, the discharge device 10 may be attached to the wall surface of the duct 2 on the front surface, or the wall surface of the duct 2 on the side surface.

The discharge device 10 includes discharging units 11 and 12, described in detail later, and a housing 20 (refer to FIG. 2 and other drawings). The housing 20 of the discharge device 10 is fixed to the wall surface of the duct 2, and disposed outside of the duct 2. The discharging units 11 and 12 are disposed inside the duct 2. These two discharging units 11 and 12 are arranged side by side in the direction perpendicular to the direction in which air flows in the duct 2 (arranged in the depth direction in FIG. 1).

During the operation of the air cleaner 100, the blower 5 and the discharge device 10 operate while receiving power supply. The discharging units 11 and 12 discharge with an application of a voltage to generate reactive species such as ions, electrons, radicals, and ozone. Ions generated by the discharging units 11 and 12 may contain positive ions only, negative ions only, or both the positive ions and the negative ions.

When the blower 5 operates, gas is sucked into the outer casing 1 through the inlet port 6, and flows into the duct 2. Gas flows upward from the bottom in the duct 2 and passes by the discharge device 10. Reactive species generated by the discharge device 10 flow toward the upper end of the duct 2 together with the gas, and flow out of the duct 2 through the first outlet 3 and the second outlet 4 to be discharged out of the air cleaner 100. The gas and the reactive species are discharged from the first outlet 3 toward the front side of the air cleaner 100. The gas and the reactive species are discharged obliquely to the rear of the air cleaner 100 from the second outlet 4.

The discharge device 10 according to the present embodiment can be used in electric machines of various different types other than the air cleaner 100. The discharge device 10 may be included in, for example, an ion generator, an air conditioner (including car-mounted air conditioner), a ventilator, a refrigerator, a washing machine, a cleaner, a dryer, a humidifier, a dehumidification machine, a hair dryer, a ceramic fan heater, or an electric fan.

[Discharge Device 10]

Figure 2:
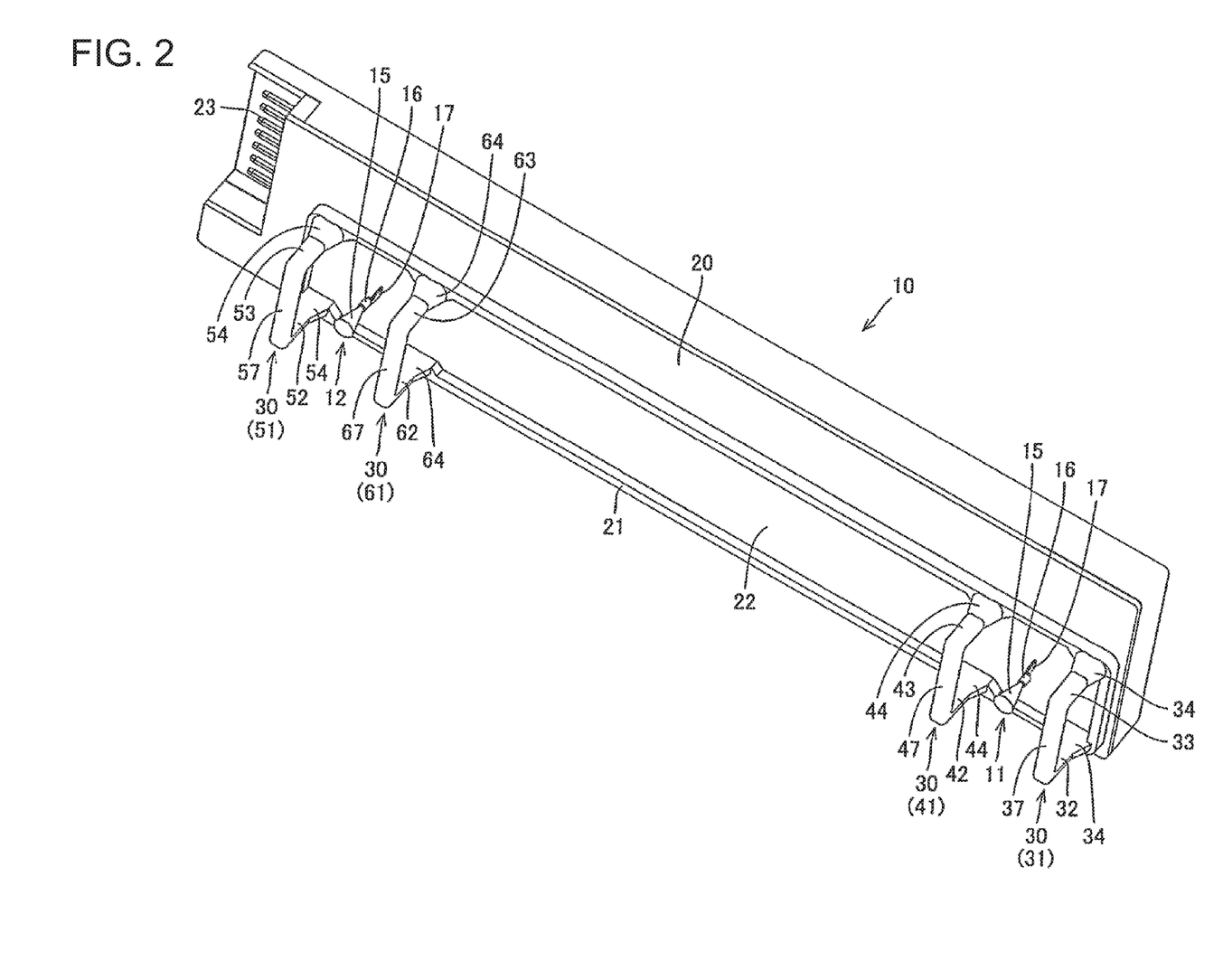
FIG. 2 is a perspective view of a discharge device according to an embodiment.
Figure 3:
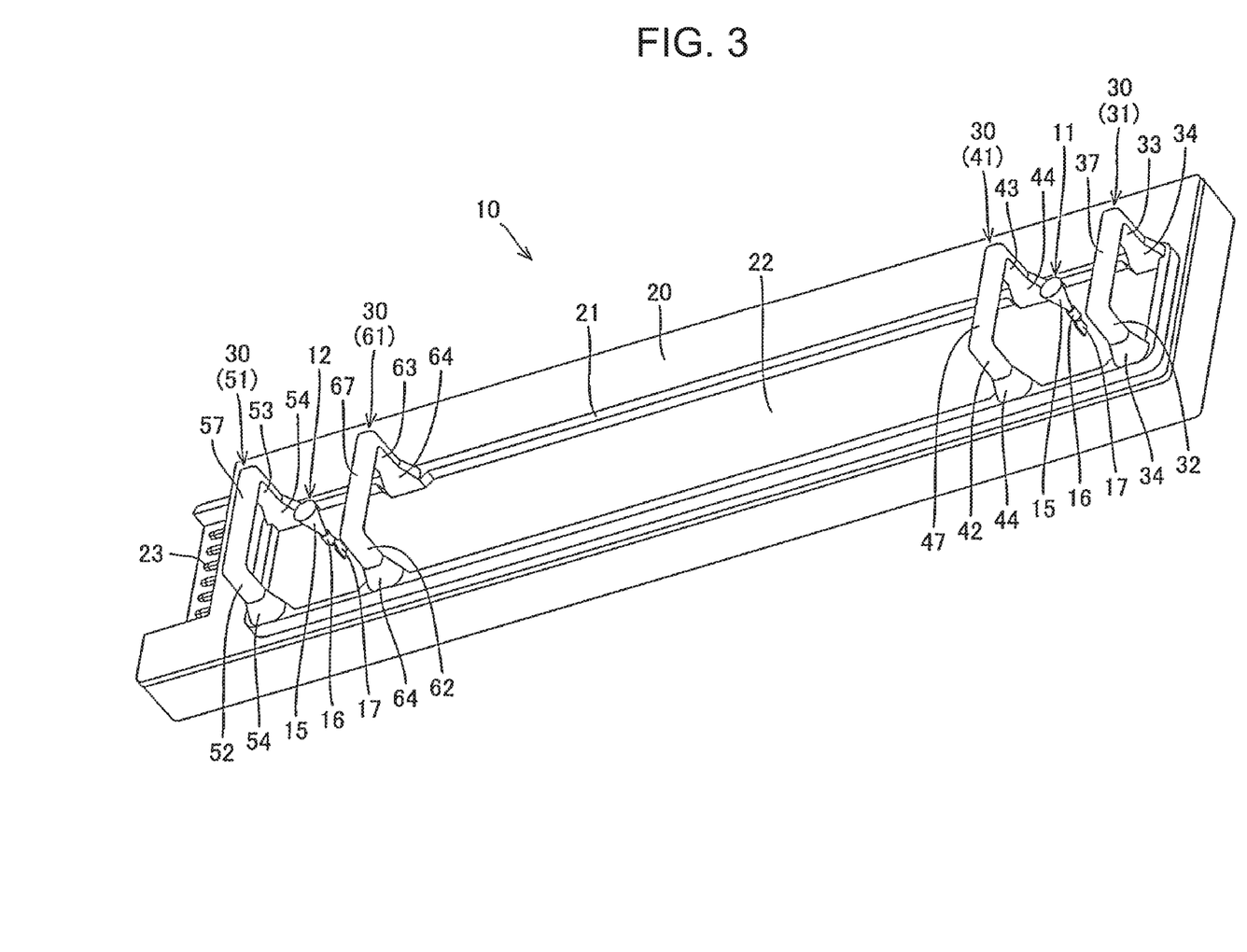
FIG. 3 is a perspective view of the discharge device illustrated in FIG. 2, viewed from a different angle.
Figure 4:
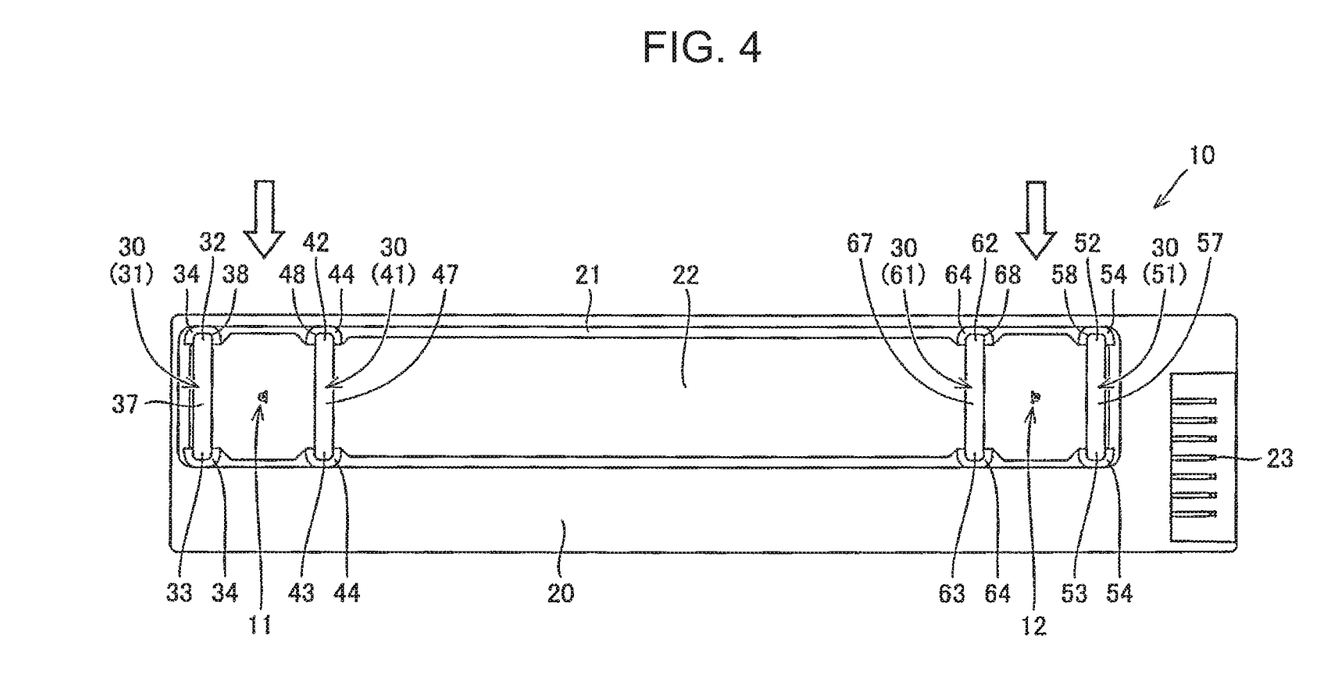
FIG. 4 is a plan view of the discharge device illustrated in FIG. 2.
Figure 5:
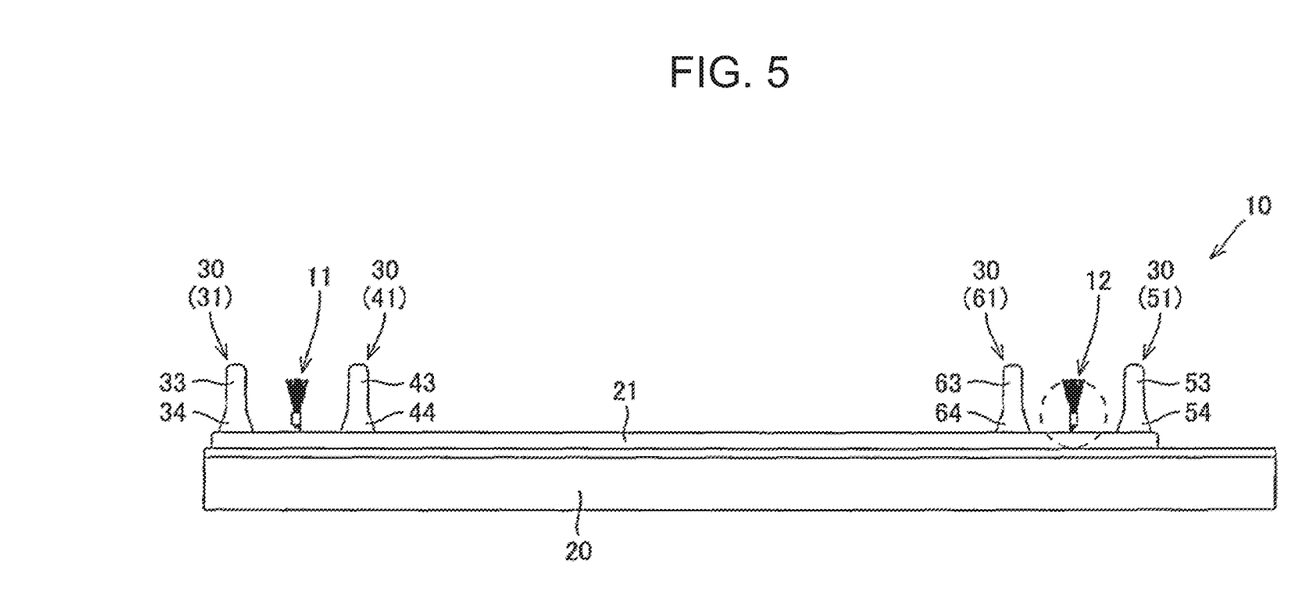
FIG. 5 is a side view of the discharge device illustrated in FIG. 2.

FIG. 2 is a perspective view of the discharge device 10 according to an embodiment. FIG. 3 is a perspective view of the discharge device 10 illustrated in FIG. 2, viewed from a different angle. FIG. 4 is a plan view of the discharge device 10 illustrated in FIG. 2. FIG. 5 is a side view of the discharge device 10 illustrated in FIG. 2.

The discharge device 10 includes the discharging units 11 and 12 and the housing 20. The discharging units 11 and 12 protrude from the housing 20. The discharging units 11 and 12 extend in the direction in which the discharging units 11 and 12 protrude from the housing 20.

The discharging units 11 and 12 include multiple electric conductors 15 with a linear shape. The linear shape includes a thread shape, a fiber shape, and a wire shape. The electric conductors 15 are formed from an electroconductive material. The electric conductors 15 may be made of, for example, metal, carbon fiber, electroconductive fiber, or electroconductive resin. The electric conductors 15 each have a base end portion, located closer to the housing 20, and a far end portion, located away from the housing 20. The far end portions of the multiple electric conductors 15 form a brush shape.

The outer diameter of each of the electric conductors 15 falls within the range of 5 μm to 30 μm. The electric conductors 15 having a thickness of larger than or equal to 5 μm have reliable mechanical strength, and less electric abrasion. The electric conductors 15 having a thickness of smaller than or equal to 30 μm bend like a hair, and easily spread and wave.

The electric conductors 15 may be formed of, for example, carbon fiber with an outer diameter of 7 μm, or electroconductive fiber made of stainless steel with an outer diameter of 12 μm or 25 μm.

The discharging units 11 and 12 each include a base portion 16 that bundles the multiple electric conductors 15. The base portion 16 has a tube shape, typically, a cylindrical tube shape. The base portion 16 is caulked while surrounding the base end portions of the multiple electric conductors 15 to support the multiple electric conductors 15 at their base end portions. The base portion 16 bundles the base end portions of the electric conductors 15.

The electric conductors 15 that protrude from the base portion 16 by a small length may fail to fully bend, and spread and wave insufficiently. To improve the discharging efficiency of the discharging units 11 and 12, the electric conductors 15 protrude from the base portions 16 by a length of larger than or equal to 3 mm. The electric conductors 15 may protrude from the base portions 16 by a length larger than or equal to 4.5 mm.

The discharging units 11 and 12 each include a support portion 17 that supports the corresponding base portion 16. The support portion 17 has a flat plate shape. The support portion 17 is supported by a substrate, not illustrated. The support portion 17 is, for example, inserted into a hole in the substrate and soldered to be fixed to the substrate. The discharging units 11 and 12 are disposed perpendicular to the substrate and fixed to the substrate. The substrate supports the discharging units 11 and 12. The discharging units 11 and 12 may be supported by the same substrate or different substrates. The support portions 17 of the discharging units 11 and 12 are in contact with the tube-shaped base portions 16 at the end portions away from the housing 20 in the longitudinal direction.

The longitudinal direction of the discharging units 11 and 12 is the direction in which the discharging units 11 and 12 protrude from the housing 20. The discharging units 11 and 12 are brush-shaped electrodes whose longitudinal direction is the direction in which they protrude from the housing 20, and each of which include multiple linear electric conductors 15 and the base portion 16 that bundles the electric conductors 15.

The housing 20 is made of an insulating resin. The housing 20 has a profile of a substantially rectangular parallelepiped box. The housing 20 has a substantially rectangular shape in a plan view in FIG. 4. The housing 20 has an angular-tube-shaped wall portion 21, which protrudes from the surface of the housing 20. The wall portion 21 has a substantially rectangular frame shape in a plan view in FIG. 4. The longitudinal direction of the housing 20 coincides with the longitudinal direction of the wall portion 21 (lateral direction in FIG. 4). The discharging unit 11 is disposed at a first end portion of the housing 20 in the longitudinal direction. The discharging unit 12 is disposed at a second end portion of the housing 20 in the longitudinal direction.

The space surrounded by the wall portion 21 constitutes a container portion. The container portion is filled with resin 22. Examples of the resin 22 include an insulating material such as epoxy resin or polyurethane resin. The housing 20 includes a connector 23 for external connection.

The resin 22 is used to insulate the substrate that supports the discharging units 11 and 12 from counter electrodes formed on the substrate. The counter electrodes are electrodes that form an electric field between themselves and the discharging units 11 and 12. The substrate is disposed inside the housing 20. The substrate and the counter electrodes are entirely covered with the resin 22 to be prevented from being exposed to the outside. The discharging units 11 and 12 are disposed perpendicularly to the surface of the resin 22. The discharging units 11 and 12 protrude from the surface of the resin 22. The discharging units 11 and 12 protrude from the housing 20.

[Electrode Protectors 30]

The discharge device 10 includes electrode protectors 30, which protect the tips of the discharging units 11 and 12. Each electrode protector 30 is disposed adjacent to a corresponding one of the discharging units 11 and 12 to prevent an object out of the discharge device 10 from directly coming into contact with the discharging unit 11 or 12. The electrode protectors 30 are integrally formed with the housing 20 to protrude from the surface of the housing 20. The electrode protectors 30 protrude further from the surface of the housing 20 than the discharging units 11 and 12. The electrode protectors 30 include a first protection portion 31 and a second protection portion 41, for the discharging unit 11, and a third protection portion 51 and a fourth protection portion 61, for the discharging unit 12.

The first protection portion 31 and the second protection portion 41 are arranged side by side in the longitudinal direction of the housing 20 with a gap interposed therebetween. Hollow arrows illustrated in FIG. 4 denote the direction of gas flow through the discharge device 10, as in FIG. 1. When viewed in the direction of gas flow, the discharging unit 11 is interposed between the first protection portion 31 and the second protection portion 41. The first protection portion 31 and the second protection portion 41 are disposed on both sides of the discharging unit 11. When the discharge device 10 is viewed in the direction of gas flow, the discharging unit 11 can be seen between the first protection portion 31 and the second protection portion 41. Openings are formed upstream and downstream of the discharging unit 11 in the direction of gas flow, not to block the gas flow to the discharging unit 11.

The third protection portion 51 and the fourth protection portion 61 are arranged side by side in the longitudinal direction of the housing 20 with a gap interposed therebetween. When viewed in the direction of gas flow, the discharging unit 12 is interposed between the third protection portion 51 and the fourth protection portion 61. The third protection portion 51 and the fourth protection portion 61 are disposed on both sides of the discharging unit 12. When the discharge device 10 is viewed in the direction of gas flow, the discharging unit 12 can be seen between the third protection portion 51 and the fourth protection portion 61. Openings are formed upstream and downstream of the discharging unit 12 in the direction of gas flow, not to prevent the gas flow to the discharging unit 12.

The openings are disposed downstream of the discharging units 11 and 12. Thus, thin long adherents adhering to the discharging units 11 and 12 are prevented from allowing the discharging units 11 and 12 to come into contact with surrounding structures with the adherents and cause leakage. Thus, the discharge device 10 is prevented from degrading its discharging performance with time. The electrode protectors 30 are disposed without covering the discharging units 11 and 12. Thus, foreign matter adhering to the discharging units 11 and 12 can be easily removed with a cleaning device such as a cotton swab.

The first protection portion 31 includes an upstream support 32, a downstream support 33, and a beam 37. The upstream support 32 and the downstream support 33 protrude perpendicularly to the surface of the housing 20. The direction in which the upstream support 32 and the downstream support 33 extend is parallel to the direction in which the discharging unit 11 extends. The upstream support 32 is disposed upstream of the discharging unit 11 in the direction of gas flow through the discharge device 10. The downstream support 33 is disposed downstream of the discharging unit 11 in the direction of gas flow. The upstream support 32 and the downstream support 33 are disposed without overlapping the discharging unit 11 in the direction of gas flow.

The beam 37 extends in the direction of gas flow. The tip end of the upstream support 32 is coupled to the upstream end of the beam 37 in the direction of gas flow. The tip end of the downstream support 33 is coupled to the downstream end of the beam 37 in the direction of gas flow. The tip ends of the upstream support 32 and the downstream support 33 protruding from the housing 20 are further apart from the housing 20 than the tip end of the discharging unit 11.

The upstream support 32 and the downstream support 33 are spaced apart from each other in the direction of gas flow. The first protection portion 31 has an arch shape. When the first protection portion 31 is viewed in the longitudinal direction of the housing 20 (lateral direction in FIGS. 4 and 5), an opening having its three sides surrounded by the upstream support 32, the downstream support 33, and the beam 37 is formed, and the discharging unit 11 can be seen through this opening.

The upstream support 32 includes a root portion 34. The root portion 34 forms an end portion of the upstream support 32 closer to the housing 20. The root portion 34 is joined to the housing 20. The upstream support 32 is joined to the housing 20 at the root portion 34. The upstream support 32 is joined to the wall portion 21 of the housing 20. The downstream support 33 similarly includes a root portion 34.

As illustrated in FIG. 4, the upstream support 32 has a curved surface 38. The curved surface 38 forms part of the surface of the upstream support 32 extending from an upstream side in the direction of gas flow toward the discharging unit 11. The curved surface 38 curves outward.

The second protection portion 41 has a similar structure as the first protection portion 31. The second protection portion 41 includes an upstream support 42, a downstream support 43, and a beam 47, and has an arch shape. The upstream support 42 and the downstream support 43 each include a root portion 44 joined to the housing 20. The upstream support 42 has a curved surface 48.

The third protection portion 51 has a similar structure as the first protection portion 31. The third protection portion 51 includes an upstream support 52, a downstream support 53, and a beam 57, and has an arch shape. The upstream support 52 and the downstream support 53 each include a root portion 54 joined to the housing 20. The upstream support 52 has a curved surface 58.

The fourth protection portion 61 has a similar structure as the first protection portion 31. The fourth protection portion 61 includes an upstream support 62, a downstream support 63, and a beam 67, and has an arch shape. The upstream support 62 and the downstream support 63 each include a root portion 64 joined to the housing 20. The upstream support 62 has a curved surface 68.

Figure 6:
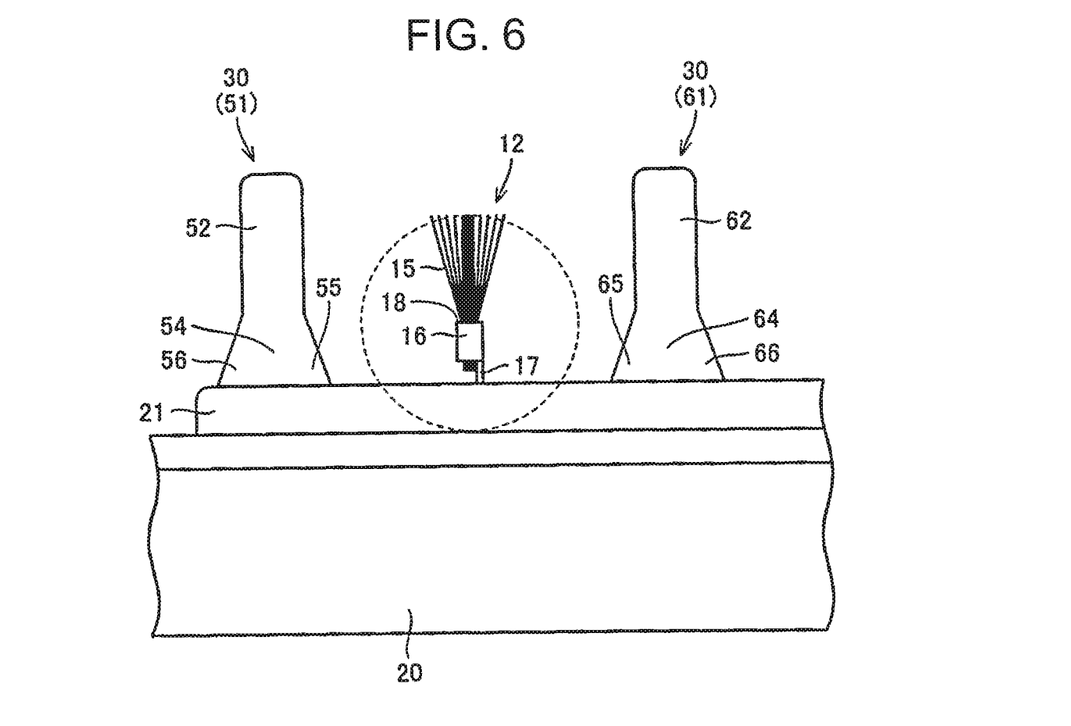
FIG. 6 is an enlarged side view of the discharge device illustrated in FIG. 5, at a portion near the discharging unit.

FIG. 6 is a side view of the discharge device 10 illustrated in FIG. 5, at a portion near the discharging unit 12 in an enlarged manner. FIG. 6 illustrates the discharging unit 12, and the third protection portion 51 and the fourth protection portion 61 with the discharging unit 12 interposed therebetween, when viewed from the upstream side in the direction of gas flow.

As illustrated in FIG. 6, the root portion 54 of the upstream support 52 of the third protection portion 51 includes a widened portion 55, which protrudes toward the discharging unit 12. The widened portion 55 makes the surface of the root portion 54 opposing the discharging unit 12 inclined with respect to the direction perpendicular to the surface of the housing 20, instead of extending in the direction perpendicular to the surface of the housing 20. The surface of the root portion 54 opposing the discharging unit 12 is inclined toward the discharging unit 12 as it extends toward the housing 20.

The root portion 54 also includes a widened portion 56, which protrudes in the direction away from the discharging unit 12. The widened portion 56 makes the surface of the root portion 54 facing away from the discharging unit 12 inclined with respect to the direction perpendicular to the surface of the housing 20, instead of extending to the direction perpendicular to the surface of the housing 20. The surface of the root portion 54 facing away from the discharging unit 12 is inclined to be further apart from the discharging unit 12 as it extends toward the housing 20.

The widened portion 55 allows the root portion 54 to be wider than the portion of the upstream support 52 other than the root portion 54. The root portion 54 has a trapezoidal shape when viewed in the direction of gas flow. Typically, the root portion 54 including the widened portions 55 and 56 has an isosceles trapezoidal shape when viewed in the direction of gas flow. The width of the root portion 54 when viewed in the direction of gas flow gradually increases as the root portion 54 extends toward the housing 20. When viewed in the direction of gas flow, the width of the root portion 54 extends to both sides, so that the strength of the upstream support 52 is improved.

In the arrangement illustrated in FIG. 1 in which the discharge device 10 is attached to the air cleaner 100, the widened portions 55 and 56 of the root portion 54 are disposed inside the duct 2.

A circle drawn with a broken line in FIG. 6 and other drawings denotes a movable range of the electric conductors 15 of the discharging unit 12. This circle has a center at a tip end 18 of the base portion 16 away from the surface of the housing 20, with the length of the electric conductors 15 by which they protrude from the base portion 16 serving as a radius. The tip end 18 of the base portion 16 is an end portion of the base portion 16 from which the electric conductors 15 protrude. The length of the electric conductors 15 by which they protrude from the base portion 16 is smaller than the length by which a structure constituted of the base portion 16 and the support portion 17 protrudes from the surface of the resin 22.

The widened portion 55 of the root portion 54 protrudes toward the discharging unit 12 to such an extent as not to interfere with the movable range of the electric conductors 15. Specifically, the entirety of the upstream support 52 including the widened portion 55 is out of the movable range of the electric conductors 15 drawn with the circle in FIG. 6. As illustrated in FIG. 6, when the discharge device 10 is viewed in the direction of gas flow, the minimum distance between the tip end 18 of the base portion 16 and the upstream support 52 is larger than the length by which the electric conductors 15 protrude from the base portion 16.

Thus, when an electric repulsive force is exerted on the electric conductors 15 in response to an application of a voltage to the discharging unit 12 and the tip ends of the brush expand, the electric conductors 15 can be prevented from coming into contact with the widened portion 55. This structure can prevent abnormal discharge and current leakage at the contact portion at which the electric conductors 15 come into contact with the upstream support 52, so that the efficiency with which reactive species are generated is reliably prevented from being reduced.

The tip end 18 of the base portion 16 and the tip ends of the widened portions 55 and 56 (tip ends of the root portion 64) away from the housing 20 are located at substantially the same position in the direction perpendicular to the surface of the housing 20. In the direction perpendicular to the surface of the housing 20, the widened portions 55 and 56 are disposed within an area closer to the housing 20 than the tip end 18 of the base portion 16. The widened portions 55 and 56 are disposed closer to the housing 20 than the tip end 18 of the base portion 16.

The downstream support 53 of the third protection portion 51 has the same structure as that of the upstream support 52. The downstream support 53 includes a root portion 54. The root portion 54 of the downstream support 53 includes a widened portion that protrudes toward the discharging unit 12, and a widened portion that protrudes away from the discharging unit 12.

The fourth protection portion 61 has the same structure as that of the third protection portion 51. The upstream support 62 of the fourth protection portion 61 includes a root portion 64. The root portion 64 includes a widened portion 65, which protrudes toward the discharging unit 12, and a widened portion 66, which protrudes away from the discharging unit 12. The downstream support 63 of the fourth protection portion 61 includes a root portion 64. The root portion 64 of the downstream support 63 includes a widened portion that protrudes toward the discharging unit 12, and a widened portion that protrudes away from the discharging unit 12.

The first protection portion 31 and the second protection portion 41 have the same structure as that of the third protection portion 51. The upstream support 32 and the downstream support 33 of the first protection portion 31 each include a root portion 34. The upstream support 42 and the downstream support 43 of the second protection portion 41 each include a root portion 44. The root portions 34 and 44 each include a widened portion that protrudes toward the discharging unit 11, and a widened portion that protrudes away from the discharging unit 11.

[Electric Circuit]

Figure 7:
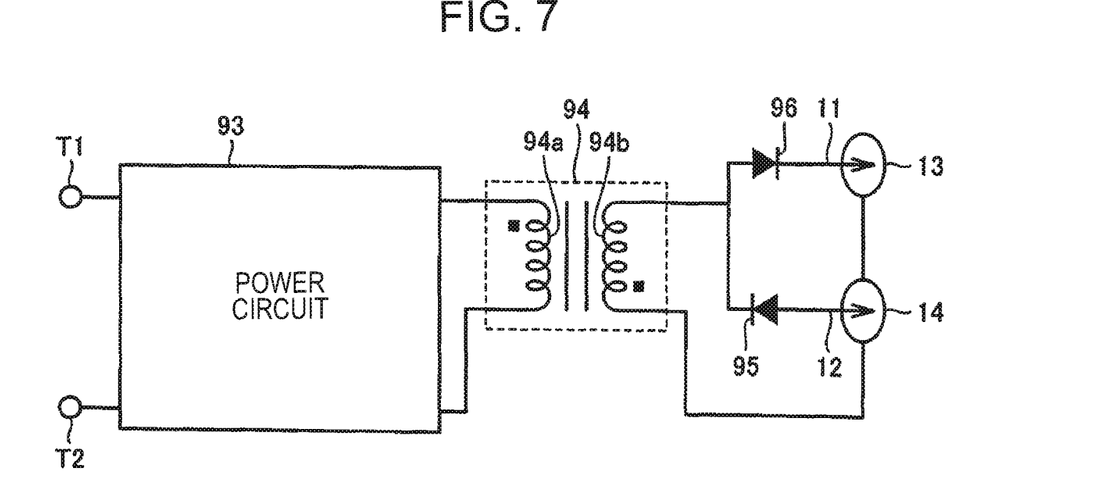
FIG. 7 is a circuit diagram of a structure of the discharge device illustrated in FIG. 2.

FIG. 7 is a circuit diagram of the structure of the discharge device 10 illustrated in FIG. 2. The discharge device 10 includes, in addition to the discharging units 11 and 12, components such as counter electrodes 13 and 14, which form an electric field between the discharging units 11 and 12, a power supply terminal T1, a ground terminal T2, diodes 95 and 96, and a step-up transformer 94. The components in the circuit illustrated in FIG. 7 other than the discharging units 11 and 12 are not illustrated in other drawings.

A positive electrode and a negative electrode of the direct-current power supply are respectively connected to the power supply terminal T1 and the ground terminal T2. The power supply terminal T1 receives a direct-current power supply voltage (for example, +12 V or +15 V), and the ground terminal T2 is grounded. The power supply terminal T1 and the ground terminal T2 are connected to the step-up transformer 94 via a power circuit 93.

The step-up transformer 94 includes a primary coil 94a and a secondary coil 94b. The secondary coil 94b has its first terminal connected to the counter electrodes 13 and 14, and its second terminal connected to the anode of the diode 96 and the cathode of the diode 95. The cathode of the diode 96 is connected to the discharging unit 11, and the anode of the diode 95 is connected to the discharging unit 12.

[Operation of Discharge Device 10]

The operation of the discharge device 10 will now be described. When a direct-current power supply voltage is applied across the power supply terminal T1 and the ground terminal T2, a capacitor (not illustrated) of the power circuit 93 is charged with electric charges. The electric charges with which the capacitor is charged are discharged via the primary coil 94a of the step-up transformer 94 to impress an impulse voltage on the primary coil 94a.

When an impulse voltage is impressed on the primary coil 94a, positive and negative high-voltage pulses are alternately impressed on the secondary coil 94b while attenuating. The positive high-voltage pulse is applied to the discharging unit 11 via the diode 96, and the negative high-voltage pulse is applied to the discharging unit 12 via the diode 95. Thus, the electric conductors 15 of the discharging units 11 and 12 cause corona discharge.

The discharging unit 11 may be, for example, a discharge electrode that generates positive ions. The discharging unit 12 may be, for example, a discharge electrode that generates negative ions. The discharging unit 11 generates positive ions by discharging in response to an application of a high voltage. The discharging unit 12 generates negative ions by discharging in response to an application of a high voltage.

The positive ions are cluster ions of multiple water molecules clustered around hydrogen ions ($H^+$), which are represented as $H^+(H_2O)_m$ (where m is any integer larger than or equal to 0). The negative ions are cluster ions of multiple water molecules clustered around oxygen ions ($O_2^-$), which are represented as $O_2^-(H_2O)_n$ (where n is any integer larger than or equal to 0). When the positive ions and negative ions are discharged into a room, both ions surround airborne mold or viruses, and cause chemical reaction with each other on their surfaces. With the effect of hydroxyl radicals (—OH), which are reactive species generated at this time, the airborne mold or another object are removed.

Figure 8:
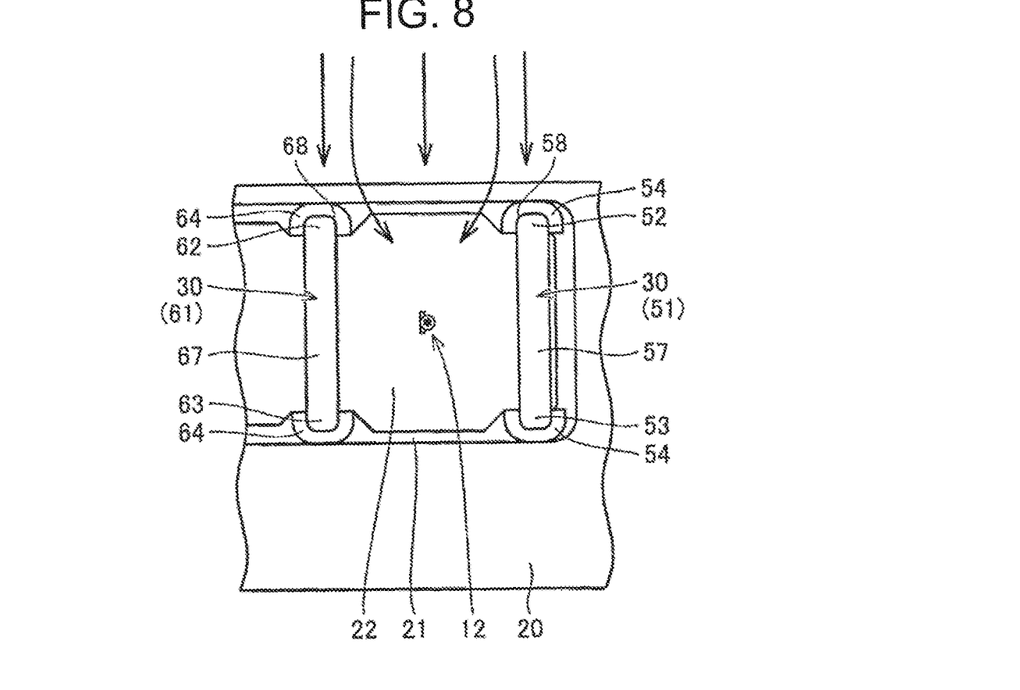
FIG. 8 is an enlarged plan view of the discharge device illustrated in FIG. 4, at a portion near the discharging unit.

FIG. 8 is a plan view of the discharge device 10 illustrated in FIG. 4, at a portion near the discharging unit 12 in an enlarged manner. Arrows illustrated in FIG. 8 denote the gas flow flowing to the discharge device 10.

The upstream support 52 of the third protection portion 51 is disposed upstream of the discharging unit 12 in the gas flow. The upstream support 52 protrudes further from the housing 20 than the discharging unit 12. The upstream support 52 has a function as a protruding unit according to an embodiment that is disposed upstream of the discharging unit 12 and protrudes further from the housing 20 than the discharging unit 12. The root portion 54 of the upstream support 52 has a widened portion 55 that protrudes toward the discharging unit 12. This widened portion 55 aligns the gas flow, so that gas flows toward the discharging unit 12, as indicated with curved arrows in FIG. 8. The root portion 54 having a larger width allows gas to more intensively flow to the movable range of the electric conductors 15.

This structure thus enables efficient transportation of negative ions generated by the discharging unit 12 with the gas flow. Prompt dispersion of generated negative ions prevents reduction of ion concentration due to neutralization between positive ions and negative ions, and reduction of ion concentration due to contact of the generated ions with the wall surface of the duct 2 (FIG. 1). Thus, the discharge device 10 according to the present embodiment can improve the efficiency of generating reactive species such as ions.

As described with reference to FIG. 6, the widened portion 55 is disposed closer to the housing 20 than the tip end 18 of the base portion 16. In the area of the widened portion 55 closer to the surface of the housing 20 than the tip end 18 of the base portion 16, the distance between the upstream support 52 and the movable range of the electric conductors 15 indicated with the broken circle in FIG. 6 is smaller. Thus, the gas that flows toward the outside of the movable range of the electric conductors 15 can be aligned with the widened portion 55 to flow toward the inside of the movable range of the electric conductors 15. This structure thus allows gas to intensively flow into the movable range of the electric conductors 15, and can improve the efficiency of generating reactive species such as ions.

As illustrated in FIG. 8, the upstream support 52 includes a curved surface 58, which curves outward from the upstream side in the direction of gas flow toward the discharging unit 12. The upstream support 52 is rounded to exclude angles to reduce pressure loss exerted on the gas flow flowing toward the discharging unit 12 through the path indicated with the curved arrows in FIG. 8. This structure thus allows gas to flow at a higher rate to the discharging unit 12, and thus can improve the efficiency of generating reactive species such as ions.

The upstream support 62 of the fourth protection portion 61 is disposed upstream of the discharging unit 12 in the gas flow. When viewed in the direction of gas flow, the discharging unit 12 is interposed between the upstream support 52 of the third protection portion 51 and the upstream support 62 of the fourth protection portion 61. The upstream support 62 protrudes further from the housing 20 than the discharging unit 12. The upstream support 62 has a function of a second protruding unit according to the present embodiment that is disposed upstream of the discharging unit 12 and protrudes further from the housing 20 than the discharging unit 12.

When viewed in the direction of gas flow, the discharging unit 12 is disposed between the upstream support 52 of the third protection portion 51 and the upstream support 62 of the fourth protection portion 61. Thus, as indicated with the curved arrows in FIG. 8, gas flows toward the discharging unit 12 from the side of the discharging unit 12 on which the third protection portion 51 is disposed, and from the side of the discharging unit 12 on which the fourth protection portion 61 is disposed. This structure allows gas to flow at a higher rate toward the discharging unit 12, and thus can further improve the efficiency of generating reactive species such as ions.

The root portion 64 of the upstream support 62 includes the widened portion 65, which protrudes toward the discharging unit 12. In addition to the widened portion 55, the widened portion 65 also aligns the gas flow. This structure thus allows gas to flow at a higher rate toward the discharging unit 12, and thus can further improve the efficiency of generating reactive species such as ions.

When viewed in the direction of gas flow, the downstream support 53 of the third protection portion 51 has the same shape as the upstream support 52. The downstream support 53 includes the root portion 54. The root portion 54 includes the widened portion that protrudes toward the discharging unit 12. When viewed in the direction of gas flow, the downstream support 63 of the fourth protection portion 61 has the same shape as the upstream support 62. The downstream support 63 includes the root portion 64. The root portion 64 includes a widened portion that protrudes toward the discharging unit 12.

To align the gas flow to effectively flow gas at a higher rate to the discharging unit 12, at least the widened portion 55, which protrudes toward the discharging unit 12, may be disposed at the upstream support 52 of the third protection portion 51. More preferably, the widened portion 65 is disposed at the upstream support 62 of the fourth protection portion 61. The downstream supports 53 and 63 disposed downstream of the discharging unit 12 do not necessarily need to have the same shape as the upstream supports 52 and 62. However, the downstream supports 53 and 63 having the same shape as the upstream supports 52 and 62 allow the discharge device 10 to be attached to the duct 2 (FIG. 1) in the reverse direction.

When the discharge device 10 illustrated in FIG. 1 is reversed, the downstream supports 53 and 63 are disposed upstream of the discharging unit 12 in the gas flow. Even when the discharge device 10 is reversed, the downstream supports 53 and 63 each including a widened portion can similarly align the gas flow to allow gas to effectively flow at a higher rate to the discharging unit 12. Thus, the air cleaner 100 can be designed highly flexibly.

Second Embodiment

Figure 9:
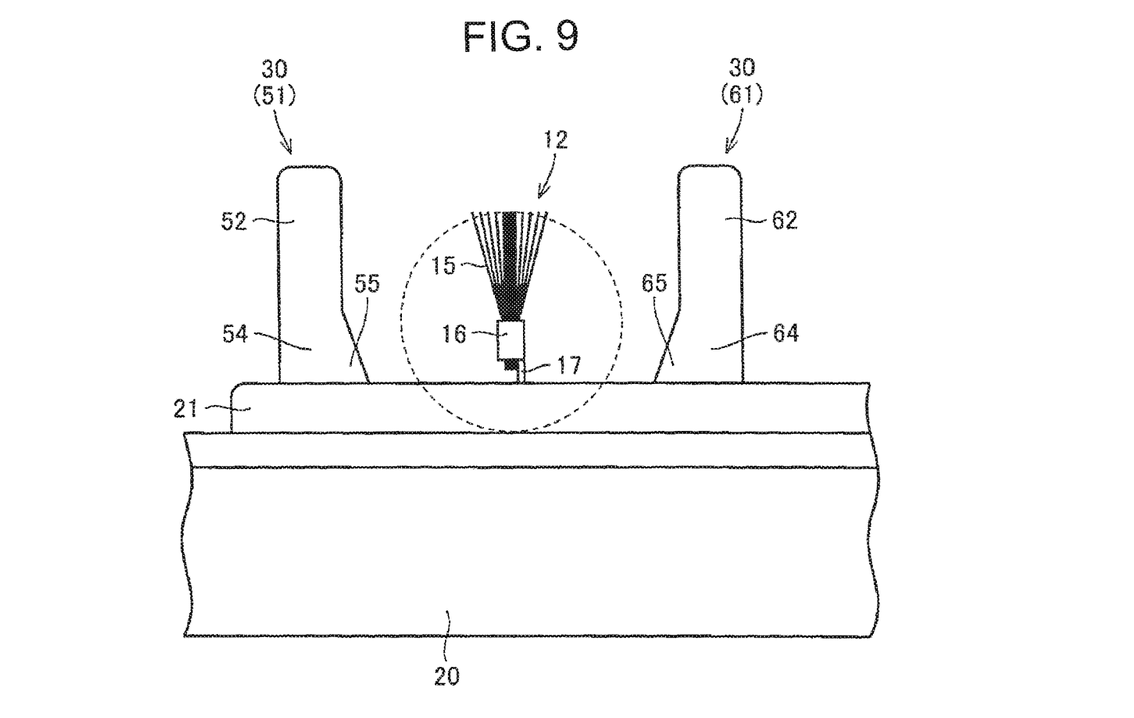
FIG. 9 is an enlarged side view of the discharge device according to a second embodiment, at a portion near the discharging unit.

FIG. 9 is a side view of a discharge device 10 according to a second embodiment, at a portion near the discharging unit 12 in an enlarged manner. In the second embodiment, the root portion 54 of the upstream support 52 of the third protection portion 51 includes the widened portion 55, which protrudes toward the discharging unit 12, but does not include a widened portion that protrudes away from the discharging unit 12. The root portion 64 of the upstream support 62 of the fourth protection portion 61 includes the widened portion 65, which protrudes toward the discharging unit 12, but does not include a widened portion that protrudes away from the discharging unit 12.

As described in the first embodiment, the widened portions 55 and 56 may be disposed on the root portion 54 of the upstream support 52 to increase the width of the root portion 54 on both sides to improve the strength of the upstream support 52. On the other hand, as illustrated in FIG. 9, in the structure not including the widened portions 56 and 66, the widened portions 55 and 65 can form the gas flow flowing toward the discharging unit 12. Intensively allowing gas to flow to the discharging unit 12 can improve the effect of generating reactive species such as ions, as in the case of the first embodiment. Compared to the first embodiment, this structure does not include the widened portions that protrude away from the discharging unit 12, so that the material required for the electrode protector 30 can be reduced, and the discharge device 10 can be lightened.

Third Embodiment

Figure 10:
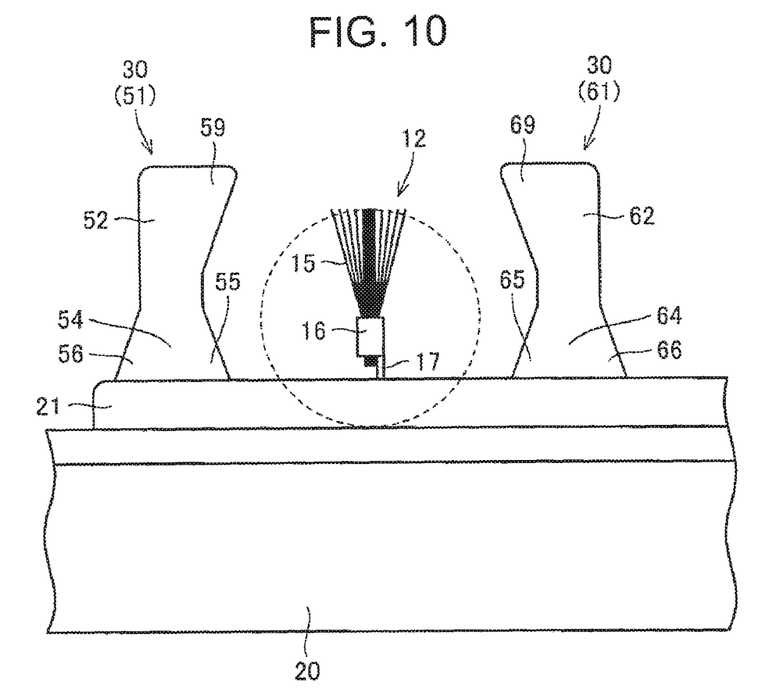
FIG. 10 is an enlarged side view of the discharge device according to a third embodiment, at a portion near the discharging unit viewed.

FIG. 10 is a side view of the discharge device 10 according to a third embodiment, at a portion near the discharging unit 12 in an enlarged manner. In the third embodiment, the upstream support 52 of the third protection portion 51 includes, in addition to the widened portion 55 at the root portion 54, an upper widened portion 59. The upstream support 62 of the fourth protection portion 61 includes, in addition to the widened portion 65 at the root portion 64, an upper widened portion 69. The upper widened portions 59 and 69 protrude toward the discharging unit 12 at a position further from the surface of the housing 20 than the tip end 18 of the base portion 16.

The upper widened portions 59 and 69 reduce the distance between the upstream support 52 and the movable range of the electric conductors 15 drawn with the broken circle in FIG. 6 in the area further from the surface of the housing 20 than the tip end 18 of the base portion 16. The widened portion 55 and the upper widened portion 59 direct the gas flowing toward the outside of the movable range of the electric conductors 15 toward the inside of the movable range of the electric conductors 15. This structure can thus allow gas to intensively flow at a higher rate to the movable range of the electric conductors 15, and can improve the efficiency of generating reactive species such as ions.

Fourth Embodiment

Figure 11:
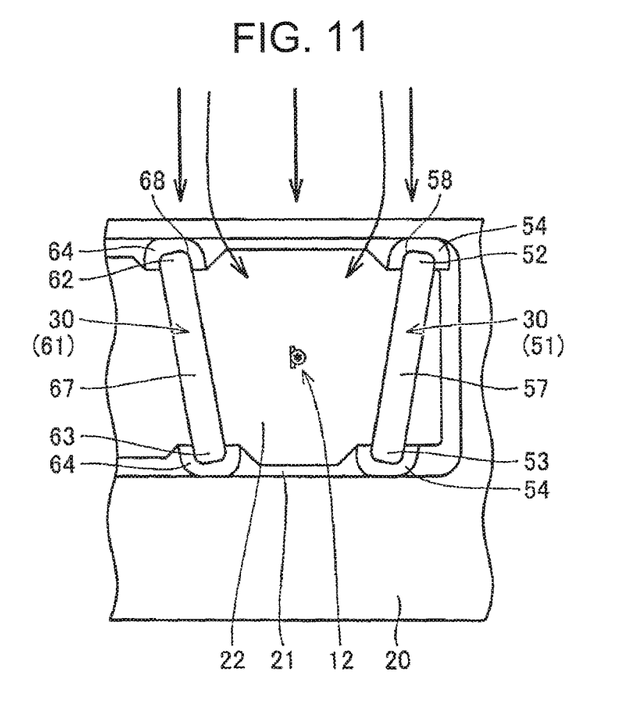
FIG. 11 is an enlarged plan view of the discharge device according to a fourth embodiment, at a portion near the discharging unit.

FIG. 11 is a plan view of a discharge device 10 according to a fourth embodiment, at a portion near the discharging unit 12 in an enlarged manner. In the first to third embodiments, the beam 57 of the third protection portion 51 and the beam 67 of the fourth protection portion 61 extend to the lateral direction of the housing 20. In the fourth embodiment, the beams 57 and 67 extend obliquely with respect to the lateral direction of the housing 20. Specifically, the beam 57 is obliquely disposed to be further from the beam 67 on the upstream side in the direction of gas flow, and to be closer to the beam 67 on the downstream side in the direction of gas flow. The beams 57 and 67 are obliquely disposed to be spaced further apart from each other on the upstream side in the direction of gas flow, and to gradually come closer to each other on the downstream side in the direction of gas flow.

In this manner, the beams 57 and 67 form a contraction duct shape when the discharge device 10 is viewed in a plan as in FIG. 11. This structure allows gas to flow at a higher rate toward the discharging unit 12, and further improves the efficiency of generating reactive species such as ions.

As described above, the widened portion 55 may have any shape that can be held within the outside of the movable range of the electric conductors 15. Thus, disposing the upstream supports 52 and 62 at positions further from the discharging unit 12 can increase the dimensions by which the widened portions 55 and 65 protrude toward the discharging unit 12. This structure allows gas to flow at a higher rate toward the discharging unit 12.

Fifth Embodiment

Figure 12:
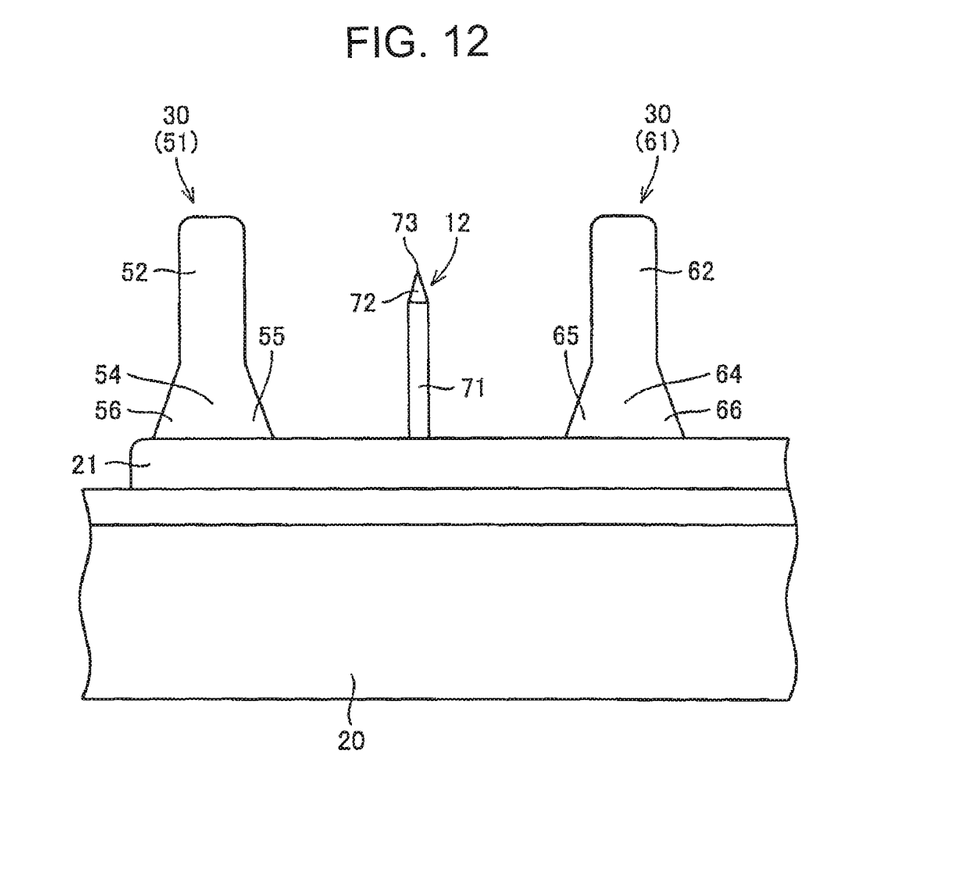
FIG. 12 is an enlarged side view of the discharge device according to a fifth embodiment, at a portion near the discharging unit.

FIG. 12 is a side view of the discharge device 10 according to a fifth embodiment, at a portion near the discharging unit 12 in an enlarged manner. In the first to fourth embodiments, the discharging units 11 and 12 have a brush-shaped structure including the linear electric conductors 15. In the fifth embodiment, a needle electrode constitutes the discharging unit 12. The discharging unit 12 according to the fifth embodiment includes a columnar portion 71, a conical portion 72, and a pointed end 73. The columnar portion 71 is fixed to the substrate. In response to an application of a high voltage to the discharging unit 12, the discharging unit 12 causes discharge at the pointed end 73 to generate ions.

Also when a needle electrode is used as the discharging unit 12, the root portions 54 and 64 of the upstream supports 52 and 62 of the third protection portion 51 and the fourth protection portion 61 disposed with the discharging unit 12 interposed therebetween include the widened portions 55 and 65 that protrude toward the discharging unit 12. This structure can form the gas flow flowing toward the discharging unit 12. As in the case of the first embodiment, this structure also has an effect of improving the efficiency of generating reactive species such as ions by causing gas to intensively flow to the discharging unit 12.

The discharging units 11 and 12 may include an electrode of a stick, linear, fiber, or sheet shape instead of a brush or needle shape.

The embodiments have been described thus far. The embodiments may be combined as appropriate. The embodiments disclosed herein should be understood as being mere examples and not limitative in all respect. The scope of the present invention is defined by the scope of claims, instead of the above description, and is intended to include the equivalents to the scope of claims, and all changes within the scope.

REFERENCE SIGNS LIST 1 outer casing
2 duct
3 first outlet
4 second outlet
5 blower
6 inlet port
7 grille
8 filter
9 fan guard
10 discharge device
11, 12 discharging unit
13, 14 counter electrode
15 electric conductor
16 base portion
17 support portion
18 tip end
20 housing
21 wall portion
22 resin
23 connector
30 electrode protector
31 first protection portion
32, 42, 52, 62 upstream support
33, 43, 53, 63 downstream support
34, 44, 54, 64 root portion
37, 47, 57, 67 beam
38, 48, 58, 68 curved surface
41 second protection portion
51 third protection portion
55, 56, 65, 66 widened portion
59, 69 upper widened portion
61 fourth protection portion
71 columnar portion
72 conical portion
73 pointed end
93 power circuit
100 air cleaner

The invention claimed is:

1. A discharge device, comprising:
a housing;
a discharging unit that protrudes from the housing and that is disposed in a duct through which gas flows, the discharging unit discharging in response to an application of a voltage; and
a protruding unit that is disposed upstream of the discharging unit in a direction in which the gas flows without overlapping the discharging unit, the protruding unit protruding further from the housing than the discharging unit,
wherein the protruding unit includes a root portion joined to the housing,
wherein the root portion includes a widened portion that is disposed in the duct and protrudes toward the discharging unit when viewed in the direction in which the gas flows, and
wherein the widened portion aligns the gas flowing through the duct, to feed the gas to the discharging unit.

2. The discharge device according to claim 1,
wherein the discharging unit includes a plurality of linear electric conductors and a base portion that bundles the plurality of linear electric conductors.

3. The discharge device according to claim 2,
wherein, when viewed in the direction in which the gas flows, a minimum distance between the protruding unit and an end portion of the base portion on a side of the base portion from which the plurality of linear electric conductors protrudes is larger than a length by which the plurality of linear electric conductors protrudes from the base portion.

4. The discharge device according to claim 2, wherein the widened portion is disposed closer to the housing than an end portion of the base portion on a side of the base portion from which the plurality of linear electric conductors protrudes.

5. The discharge device according to claim 1, wherein a surface of the protruding unit curves from an upstream side in the direction in which the gas flows toward the discharging unit to protrude outward.

6. The discharge device according to claim 1, wherein the root portion includes a second widened portion that protrudes away from the discharging unit when viewed in the direction in which the gas flows.

7. The discharge device according to claim 1, further comprising:
a second protruding unit that is disposed while having the discharging unit interposed between the second protruding unit and the protruding unit when viewed in the direction in which the gas flows, the second protruding unit protruding further from the housing than the discharging unit.

8. An electric machine, comprising:
the discharge device according to claim 1; and
a blower that feeds gas to the discharge device.

* * * * *